United States Patent
Caplan et al.

[11] Patent Number: 5,960,140
[45] Date of Patent: Sep. 28, 1999

[54] QUICK-RELEASE CONNECTOR FOR FIBEROPTIC CABLES

[75] Inventors: Charles H. Caplan; Frederick N. Bushroe; Anthony R. Ford, all of Tucson, Ariz.

[73] Assignee: Surgical Acuity, Inc., Madison, Wis.

[21] Appl. No.: 08/807,718

[22] Filed: Feb. 28, 1997

Related U.S. Application Data

[60] Provisional application No. 60/012,608, Mar. 1, 1996.
[51] Int. Cl.⁶ ........................................................ G02B 6/36
[52] U.S. Cl. ........................................................... 385/87
[58] Field of Search ............................. 385/86, 87, 56, 385/57, 58, 60, 62, 66, 67, 68, 76, 77, 78, 79, 81

[56] References Cited

U.S. PATENT DOCUMENTS

| | | | |
|---|---|---|---|
| 3,631,597 | 1/1972 | Lieb et al. | 433/129 |
| 3,638,013 | 1/1972 | Keller | 433/31 |
| 3,668,612 | 6/1972 | Nepovim | 439/584 |
| 3,671,926 | 6/1972 | Nepovim | 439/584 |
| 3,735,492 | 5/1973 | Karter et al. | 433/90 |
| 3,798,776 | 3/1974 | Lentine et al. | 433/129 |
| 3,813,782 | 6/1974 | Nilles et al. | 433/129 |
| 3,846,738 | 11/1974 | Nepovim | 439/584 |
| 3,969,823 | 7/1976 | Nakanishi | 433/122 |
| 4,020,556 | 5/1977 | Sotman | 439/29 |
| 4,292,027 | 9/1981 | Richmond | 433/127 |
| 4,304,552 | 12/1981 | Wright et al. | 433/126 |
| 4,315,744 | 2/1982 | Albert | 433/126 |
| 4,377,292 | 3/1983 | Staron | 279/46.1 |
| 4,676,577 | 6/1987 | Szegda | 439/584 |
| 4,762,017 | 8/1988 | Jaksic | 74/500.5 |
| 4,779,949 | 10/1988 | Iri et al. | 385/87 |
| 4,799,400 | 1/1989 | Pickell | 74/502.6 |
| 4,812,006 | 3/1989 | Osborn et al. | 385/69 |
| 4,854,893 | 8/1989 | Morris | 439/578 |
| 4,923,412 | 5/1990 | Morris | 439/578 |
| 4,952,174 | 8/1990 | Sucht et al. | 439/584 |
| 4,964,685 | 10/1990 | Savitsky et al. | 385/58 |
| 4,979,911 | 12/1990 | Spencer | 439/583 |
| 5,000,465 | 3/1991 | Seele | 279/133 |
| 5,011,432 | 4/1991 | Sucht et al. | 439/584 |
| 5,040,979 | 8/1991 | Kuhn | 433/126 |
| 5,055,044 | 10/1991 | Kuhn | 433/126 |
| 5,074,789 | 12/1991 | Shibata | 433/129 |
| 5,090,906 | 2/1992 | Pernot | 433/127 |
| 5,139,421 | 8/1992 | Verderber | 433/31 |
| 5,211,560 | 5/1993 | Lowder et al. | 433/166 |
| 5,297,972 | 3/1994 | McMills et al. | 439/133 |
| 5,348,319 | 9/1994 | Stolzer | 279/77 |
| 5,383,785 | 1/1995 | Brugger | 433/129 |
| 5,417,692 | 5/1995 | Goble et al. | 606/73 |

Primary Examiner—Hung N. Ngo
Attorney, Agent, or Firm—DeWitt Ross & Stevens S.C.

[57] ABSTRACT

A connector for removably attaching fiberoptic cables to light-transmitting implements such as translucent probes and projection optics is shown and described. A tube is provided with a sleeve which may be fit over the tube. With the sleeve partially fit over the tube, the cable may be inserted in one end of the tube and the implement in the other end. When the sleeve is then pulled or threaded more fully over the tube, tongues provided on the tube move into engagement with the implement and fingers on the tube are locked in place against the cable.

21 Claims, 7 Drawing Sheets

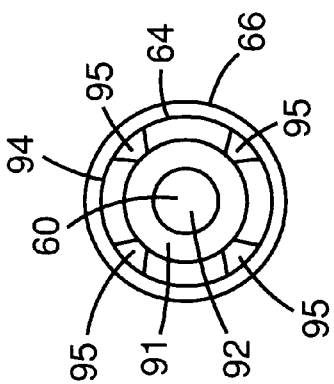
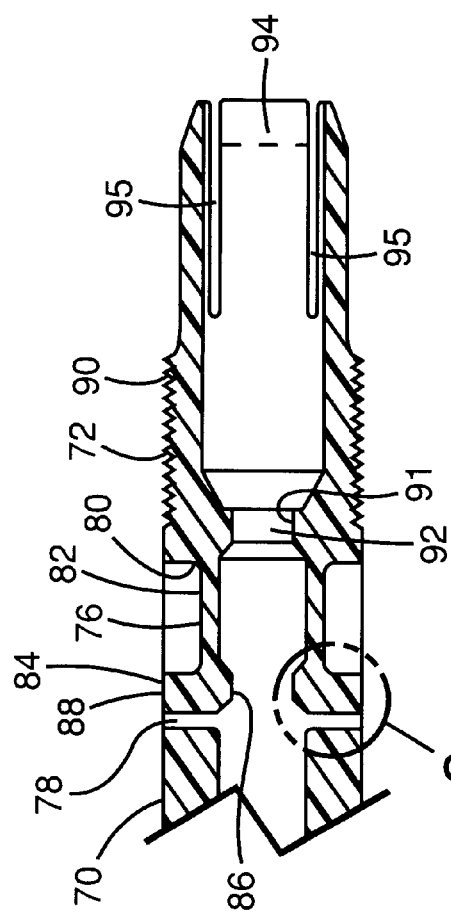
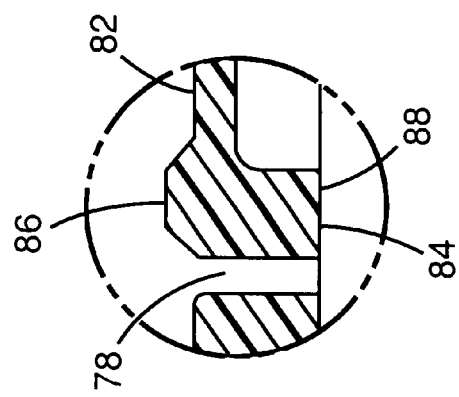

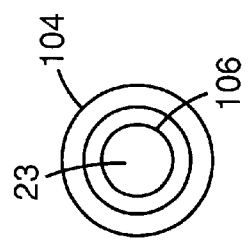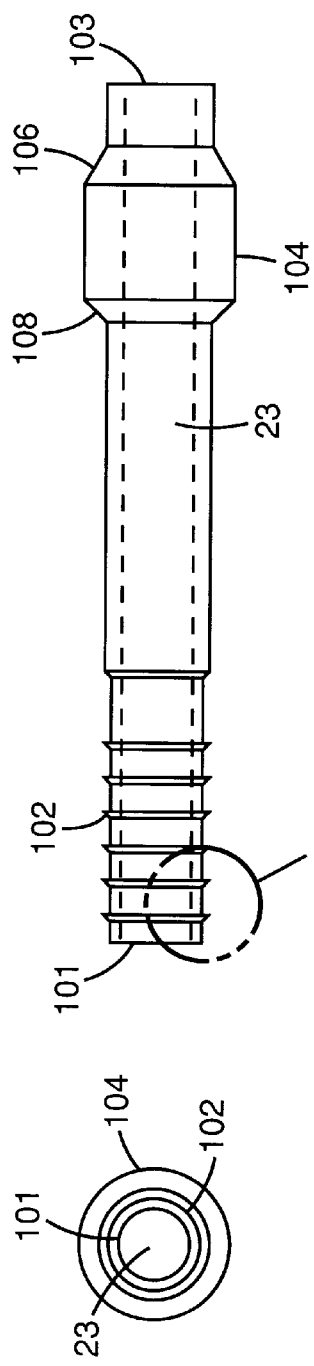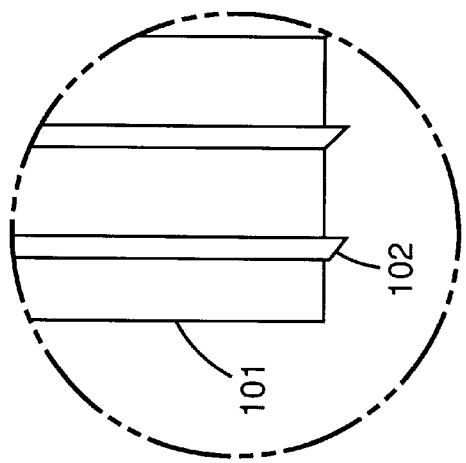

QUICK-RELEASE CONNECTOR FOR FIBEROPTIC CABLES

CROSS REFERENCE TO RELATED APPLICATIONS

This application claims priority under 35 USC §119(e) to U.S. Provisional Patent Application 60/012,608 filed Mar. 1, 1996, the entirety of which is incorporated by reference herein.

FIELD OF THE INVENTION

The present invention relates to a quick-release connector for connecting the terminal end of a fiberoptic cable to an implement which emits or otherwise uses light transmitted from the fiberoptic cable, e.g., light-transmitting probes (transilluminators), mirrors, projection optics, etc.

BACKGROUND OF THE INVENTION

Numerous illumination implements (transilluminators, etc.) in medical and dental fields utilize fiberoptic cables to carry light from a remotely-located light source to the implement, which then emits or further transmits the light. There is a need for a small, lightweight, easy-to-use connection apparatus which firmly (but removably) affixes fiberoptic cables to light-transmitting implements in a manner which protects the juncture between the cable and implement from fouling by bodily fluids or other substances, and which simultaneously maintains high light transmission efficiency at thus juncture.

SUMMARY OF THE INVENTION

The invention, which is defined by the claims set out at the end of this disclosure, is directed to a cable connector including a tube and a sleeve. The tube includes at least two resiliently flexible tongues extending from one end of the tube. A resiliently flexible finger has an end attached to the tube at a location spaced from the tongues. A fiberoptic cable may be inserted within the tube and adjacent the finger, and an implement may be inserted within the tube and between the tongues. By then inserting the tube within the sleeve, the tongues are biased inwardly into engagement with the implement and the finger is locked into place bearing against the cable. The cable and implement are thereby firmly fixed in coaxial relationship within the tube, thereby maintaining high efficiency light transmission between the cable and implement. The cable and/or implement may be rapidly removed by removing the tube from the sleeve so that the tongues and finger are free to release the implement and cable. A handle may be included on the tube to allow the user to position the implement as desired.

As examples of the application of the invention, the quick-release connector can be used to connect the terminal end of a fiberoptic cable to illuminated dental mirrors, illuminating probes (transilluminators), illuminating loupes, and similar light-utilizing implements. The quick-release connector is intended to provide an especially strong and durable connection between the cable and the implement so that tension on the fiberoptic cable will not cause its terminal end to release from the implement. The quick-release connector is also intended to maintain high light transmission efficiency between the terminal end of the fiberoptic cable and the implement by maintaining the cable and implement in close axially-aligned relation. The connector also protects the juncture between the terminal end of the cable and the implement from fouling by bodily fluids or other substances.

BRIEF DESCRIPTION OF THE DRAWINGS

FIG. 7 is a partial sectional view shown from the line 7—7 of FIG. 3.

FIG. 8 is a top view of the tube of FIG. 2.

FIG. 9 is an enlarged partial view of a portion of the tube of FIG. 7.

FIG. 13 is a side view of the terminal connector of the fiberoptic cable of FIG. 1.

FIG. 14 is a bottom view of the terminal connector of FIG. 13.

FIG. 15 is a top view of the terminal connector of FIG. 13.

FIG. 16 is an enlarged partial view of a portion of the terminal connector of FIG. 13.

DETAILED DESCRIPTION OF THE PREFERRED EMBODIMENTS

Figure 1:
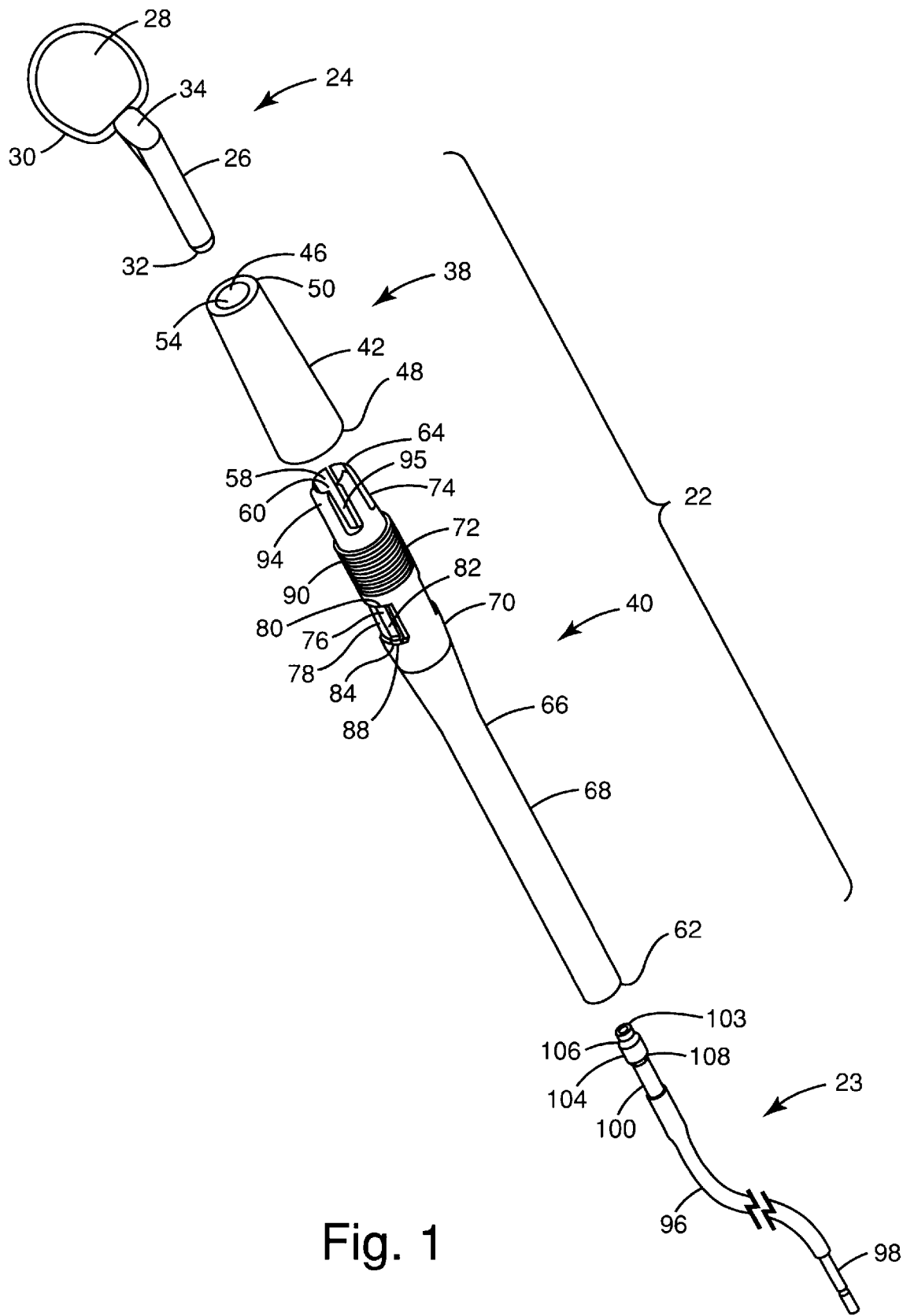
FIG. 1 is an exploded perspective view of the connector of the present invention, shown with a dental mirror and a fiberoptic cable.
Figure 2:
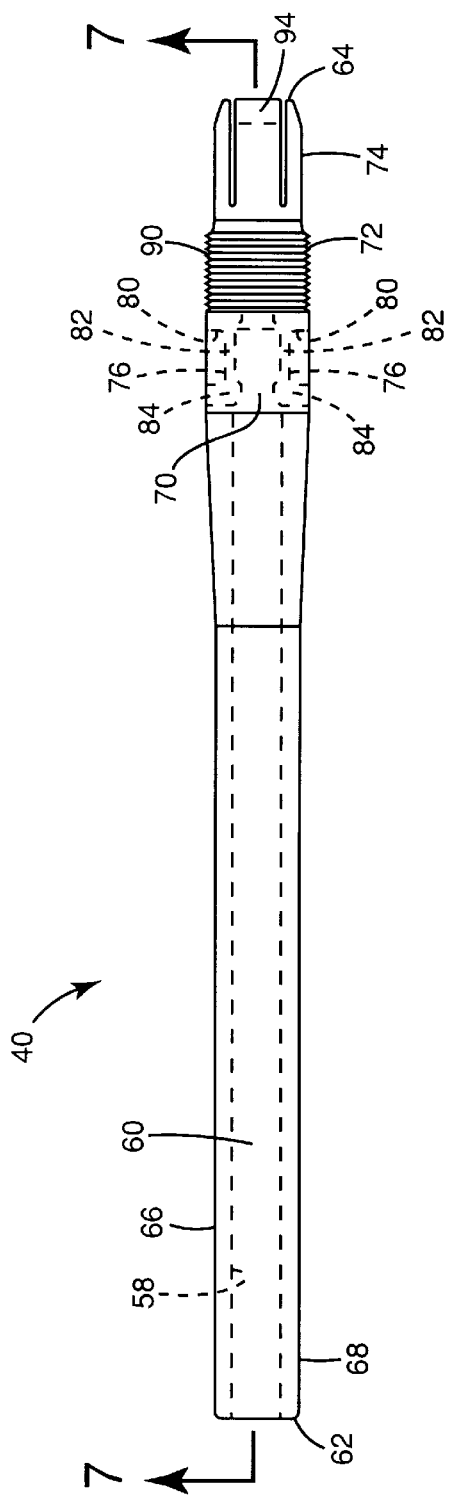
FIG. 2 is a side view of the tube of the connector of FIG. 1.
Figure 3:
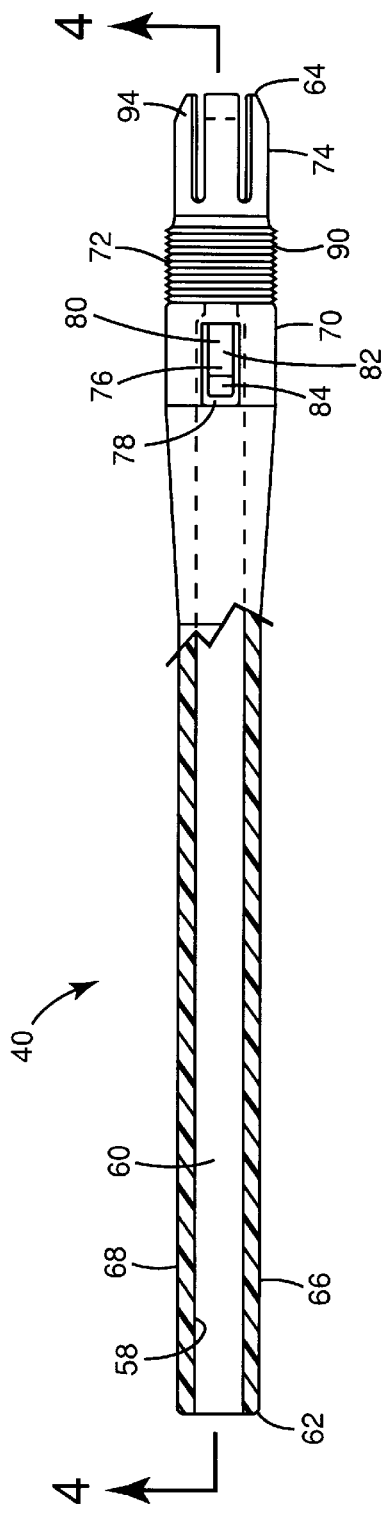
FIG. 3 is a partial side view of the tube, shown axially rotated 90° from FIG. 2.
Figure 5:
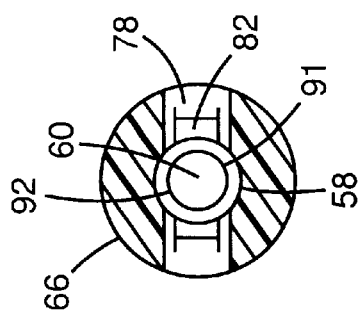
FIG. 5 is a sectional view of the tube as shown at the line 5—5 of FIG. 4.

Throughout the figures, wherein the same features are identified with the same reference numbers throughout, a preferred embodiment of the connector of the present invention is shown in FIG. 1 at the reference number 22. Also shown in FIG. 1 are a fiberoptic cable 23 and a dental mirror 24, both of which may be used in combination with the connector 22. Each of the dental mirror 24, the connector 22, and the fiberoptic cable 23 will now be discussed in turn.

The dental mirror 24, which generally includes a mirror shank 26 and a mirror 28 retained within a mirror frame 30, is designed to allow transmission of light from the fiberoptic cable 23 through the mirror shank 26 so that areas around the mirror 28 may be illuminated. An exemplary dental mirror 24 is described in U.S. Pat. No. 5,139,421 to Verderber. The Verderber mirror includes a generally translucent mirror shank 26 having a shank end 32. When light enters the shank end 32 from the fiberoptic cable 23, it is transmitted through the mirror shank 26 to exit a shank heel 34. The light is simultaneously internally reflected from the shank heel 34 to exit a shank face (not shown) located immediately adjacent the mirror 28. Other exemplary forms of alternate mirrors and other implements suitable for use with the connector 22 will be discussed below.

Figure 12:
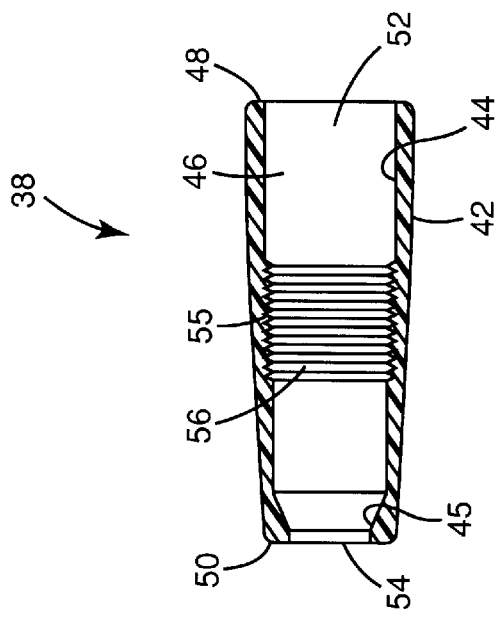
FIG. 12 is a side sectional view of the collet sleeve of FIG. 10.
Figure 11:
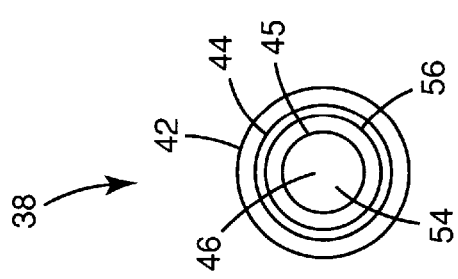
FIG. 11 is a bottom view of the collet sleeve of FIG. 10.
Figure 10:
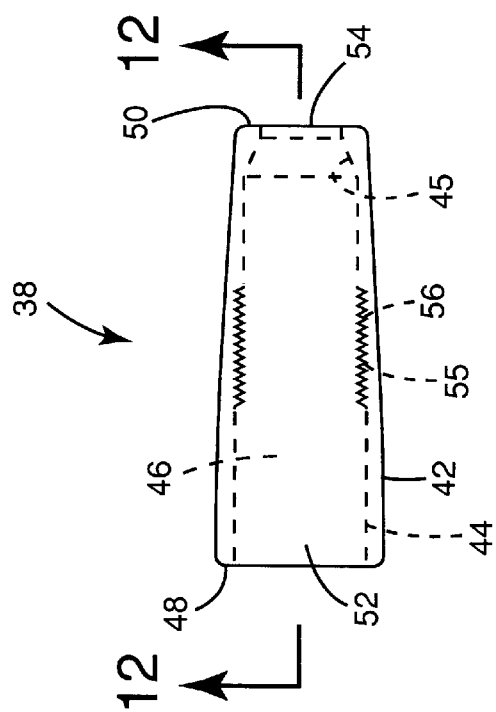
FIG. 10 is a side view of the collet sleeve of the connector of FIG. 1.

As illustrated in FIG. 1, the connector 22 has a collet sleeve 38 and a tube 40, each of which are preferably made out of plastic material. FIGS. 10-12 illustrate the collet sleeve 38 in greater detail. As illustrated particularly by FIG. 12, the collet sleeve 38 includes an external collet sleeve surface 42 and an internal collet sleeve surface 44 which has a converging tip portion 45 near its tip. The internal collet sleeve surface 44 defines an axial collet sleeve passage 46 which extends from a collet sleeve tail 48 to a collet sleeve tip 50 adjacent the converging tip portion 45. At the collet sleeve tail 48, the collet sleeve passage 46 opens upon a tube insertion passage 52 which is sized to receive the tube 40 of the connector 22. At the tip 50 of the collet sleeve 38, the collet sleeve passage 46 opens onto a mirror shank aperture 54 which is sized to receive the mirror shank 26. An attachment area 55 bearing threads 56 is provided on the internal collet sleeve surface 44 between the converging tip portion 45 and the collet sleeve tail 48. As will be discussed below, the tube 40 includes collet sleeve attachment means for releasably attaching the tube 40 to the internal collet sleeve surface 44 of the collet sleeve 38. Part of this collet sleeve attachment means may be provided by threading 56 located on the internal collet sleeve surface 44.

The tube 40, which is shown in detail in FIGS. 2–9, has a tube interior surface 58 defining an axially oriented cable passage 60. The cable passage 60 extends from a proximal end 62 of the tube 40 to a distal end 64 of the tube 40. The tube 40 also has a tube exterior surface 66 which includes a handle 68 at the proximal end 62, a cable engagement portion 70, a collet sleeve engagement portion 72, and a implement engagement portion 74 at the distal end 64. Each of these portions of the tube 40 will now be discussed in turn.

The handle 68, which is adapted to be gripped by a human hand, is preferably textured for a comfortable and firm grip. The handle 68 may include finger ridges, high-friction sleeves, or other means known to the art for enhancing its grippability. As will be discussed below, the handle 68 is an optional part of the connector 22, and is only needed when a grippable wand is desired at the end of the connector 22.

The cable engagement portion 70, shown particularly in FIGS. 4–9, includes cable engagement means for engaging the end of the fiberoptic cable 23 The cable engagement means are preferably in the form of one or more fingers 76, each of which is defined by a generally U-shaped slot 78 extending from the tube exterior surface 66 to the tube interior surface 58. Each finger 76 has an anchor end 80 integrally attached to the tube 40, a resilient flexible intermediate segment 82, and a floating end 84 which is bounded along the circumference of the tube 40 by the slot 78 and the intermediate segment 82 of the finger 76. The intermediate segment 82 maintains the floating end 84 of the finger 76 in spring-biased relation to the anchor end 80 of the finger 76. As best illustrated by FIG. 9, the floating end 84 of each finger 76 has an inner raised terminal projection 86 at the tube interior surface 58, and an outer terminal surface 88 flush with the tube exterior surface 66. When the finger 76 is unloaded, i.e., unbent, the inner raised terminal projection 86 at the floating end 84 is radially spaced further inward than the surrounding area on the tube interior surface 58.

The collet sleeve engagement portion 72 bears collet sleeve attachment means for releasably attaching the tube exterior surface 66 to the collet sleeve 38. As illustrated by FIGS. 1–4 and 7, these collet sleeve attachment means are preferably in the form of tube threading 90 capable of engaging collet sleeve threading 56.

Figure 4:
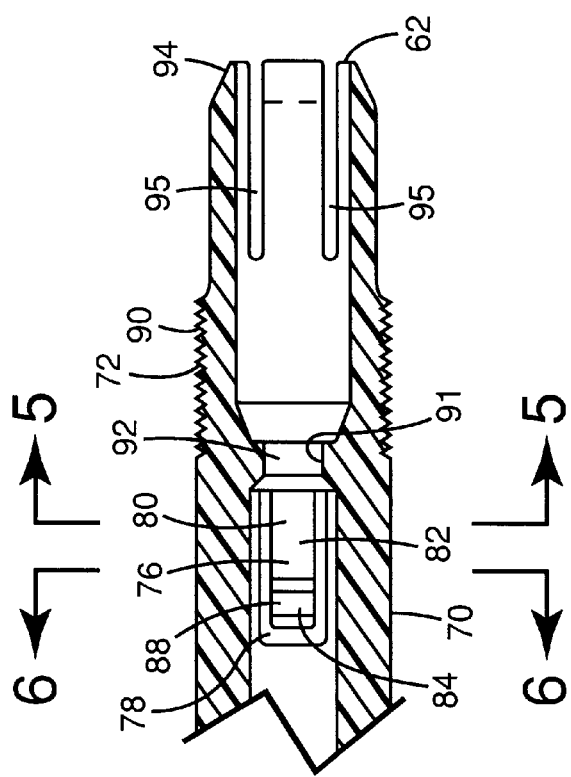
FIG. 4 is a partial sectional view of the tube shown from the line 4—4 of FIG. 2.
Figure 6:
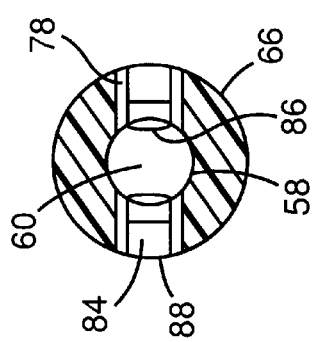
FIG. 6 is a sectional view of the tube shown along the line 6—6 of FIG. 4.

As best shown by FIGS. 4 and 7, the tube interior surface 58 is radially inwardly narrowed by a protrusion or converging portion 91 at the juncture between the collet sleeve engagement portion 72 and the cable engagement portion 70, thereby forming an annular narrowed throat 92. This narrowed throat 92 will be discussed at greater length below.

The implement engagement portion 74 of the tube 40 includes shank engagement means for releasably engaging the mirror shank 26, or the shank of a different implement. As illustrated by FIGS. 1–4 and 7, the shank engagement means is preferably provided by at least two resilient flexible tongues 94 defined by slots 95 on the implement engagement portion 74. When the collet sleeve 38 engages the collet sleeve engagement portion 72 of the tube 40, the converging tip portion 45 of the internal collet sleeve surface 44 contacts the tongues 94 and bends them radially inward.

As shown by FIG. 1, the fiberoptic cable 23—which may be a single-strand or multi-strand fiber having either a solid or liquid core—has a protective sheath 96 and an end plug 98 for plugging into a light source. Both the sheath 96 and the end plug 98 are known to the art. The fiberoptic cable 23 also includes a terminal connector 100, which is illustrated in greater detail in FIGS. 13–16. The terminal connector 100, which is preferably made of metal, is generally tubular and is sized so that the fiberoptic cable 23 may be retained therein. The fiberoptic cable 23 is inserted within a connector tail 101, and the connector tail 101 is in turn inserted within the sheath 96 and retained therein by ridges 102. The opposite end of the terminal connector 100 includes an open connector tip 103 where the fiberoptic cable 23 is exposed to allow emission of light. A barrel 104 is located adjacent the connector tip 103. The barrel 104 includes a barrel tip 106 immediately adjacent the connector tip 103, and an opposing barrel base 108. The connector tip 103 and barrel 104 are sized so that when the terminal connector 100 is fit within the cable passage 60 at the tube proximal end 62, the connector tip 103 closely fits within the narrowed throat 92, and the barrel 104 closely fits between the narrowed throat 92 and the inner raised terminal projection 86 of each finger 76. As will be discussed shortly, the barrel 104 cooperates with the fingers 76 of the cable engagement portion 70 to form the cable engagement means.

The operation of the connector 22 may be described as follows. With the collet sleeve 38 removed from the tube 40 or, more precisely, loosened to expose the outer terminal surface 88 of the fingers 76, the terminal connector 100 of the fiberoptic cable 23 is inserted into the tube proximal end 62 until the barrel 104 encounters the inner raised terminal projection 86 on each finger 76. The fiberoptic cable 23 may then be further inserted so that the barrel 104 pushes against the inner raised projections 86 and pushes each finger 76 radially outward. The intermediate segment 82 of the fingers 76 is flexible enough that the fingers 76 are easily biased radially outward by the axial insertion of the barrel 104, even though the cable 23 is not very rigid. With further insertion, the connector tip 103 slips into the narrowed throat 92 so that the barrel 104 fits between the narrowed throat 92 and the inner raised terminal projection 86 of each finger 76. The resiliently flexible fingers 76 then snap inward so that the inner raised terminal projection 86 of each finger 76 abuts the barrel base 108. At this point, the fiberoptic cable 23 is firmly secured within the tube 40 by the action of the fingers 76. However, a gentle tug on the fiberoptic cable 23 will cause the fingers 76 to release the barrel 104 and allow removal of the fiberoptic cable 23.

The tube proximal end 62 is then inserted within the tube insertion passage 52 of the collet sleeve 38. The mirror shank 26 is inserted within the mirror shank aperture 54 at the collet sleeve tip 50. The mirror shank 26 is simultaneously inserted within the cable passage 60 and between the tongues 94 at the implement engagement portion 74. The collet sleeve 38 is attached to the collet sleeve engagement portion 72 by rotatably engaging the collet sleeve threading 56 with the tube threading 90. This causes the internal collet sleeve surface 44 (more specifically, the converging tip portion 45) to spring-bias the tongues 94 radially inward so that they engage the mirror shank 26. Further insertion of the tube 40 within the collet sleeve 38 moves the internal collet sleeve surface 44 into abutment with the outer terminal surface 88 of each finger 76, thereby preventing the fingers 76 from moving radially outward. As a result, so long as the collet sleeve 38 is affixed at least past the outer terminal surface 88 of the collet sleeve engagement portion 72 of the tube 40, the fingers 76 cannot release the barrel 104 of the fiberoptic cable 23. Advantageously, the collet sleeve 38 also covers the slot 78, thereby preventing contamination of the collet sleeve passage 46 and the rest of the interior of the connector 22.

With the dental mirror 24 and the fiberoptic cable 23 firmly affixed within the connector 22, the connector 22 is ready for use. The handle 68 is grasped by the hand, the light source is activated to supply light through the shank heel 34, shank face 36, and/or other parts of the dental mirror 24, and the apparatus is used in the manner known to the art. The connector 22 securely holds the dental mirror 24 and fiberoptic cable 23 so that they cannot be dislodged from the connector 22 during use, and so that high light transmission efficiency between the fiberoptic cable 23 and the dental mirror 24 is maintained. By partially withdrawing the tube 40 from the collet sleeve 38 so that the outer terminal surface 88 of the fingers 76 are exposed so that the fiberoptic cable 23 is removable, but the mirror shank 26 will still be grasped by the tongues 94. Further withdrawal of the tube 40 will relax the tongues 94 and allow removal of the mirror shank 26.

The invention encompasses numerous modifications and enhancements to the embodiment described above. Several of such modifications will now be described for the purpose of illustration, it being understood that the invention is not limited only by the claims at the end of this disclosure.

First, collet sleeve attachment means other than the threading 90 may be used to effect engagement between the internal collet sleeve surface 44 and the collet sleeve engagement portion 72. The collet sleeve attachment means may also be achieved by a frictional fit between the collet sleeve 38 and tube 40, mating protrusions and indentations on the internal collet sleeve surface 44 and tube exterior surface 66, or a combination of any of these means.

Second, the cable engagement means may utilize structures other than a barrel 104 to effect engagement between the fingers 76 and the terminal connector 100. The fingers 76 may be designed to engage any discontinuity in the terminal connector 100. For example, the terminal connector 100 may include a notch or annular valley wherein the inner raised terminal projection 86 of one or more fingers 76 may fit.

Figure 17:
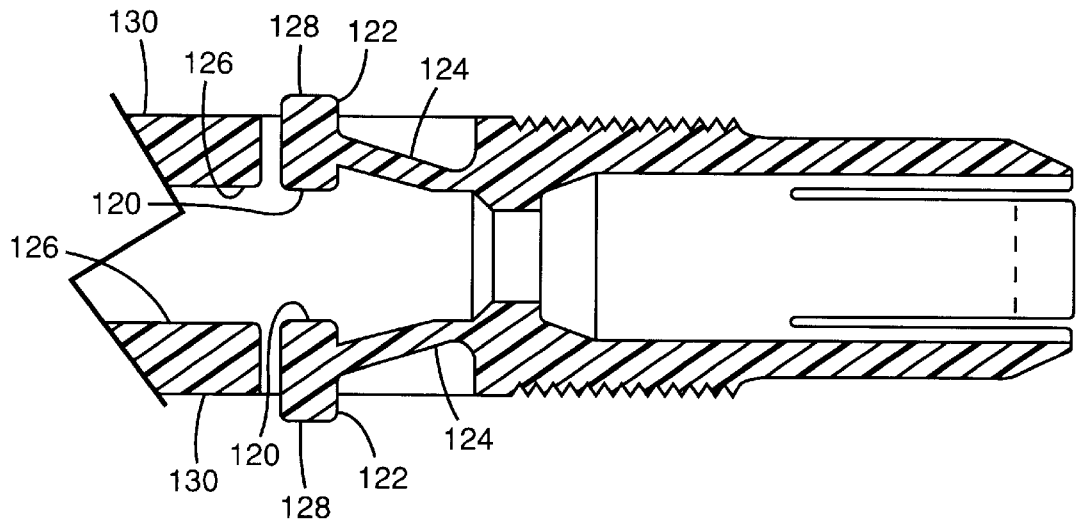
FIG. 17 is a partial side sectional view of an alternate embodiment of a tube.

Third, it is understood that in different embodiments of the connector 22, the floating ends 84 of the unloaded fingers 76 can be radially spaced from the axis of the tube 40 at locations different from those illustrated in FIGS. 1–9. For example, as illustrated in FIG. 17, the inner raised projection 120 of the floating end 122 of the finger 124 may be flush with the tube interior surface 126, and the outer terminal surface 128 can be raised in relation to the tube exterior surface 130. In this embodiment, the inner raised projection 120 will not engage the barrel 104 until the internal collet sleeve surface 44 engages the outer end surface 128 of the finger 124 and pushes the finger 124 inward.

Figure 18:
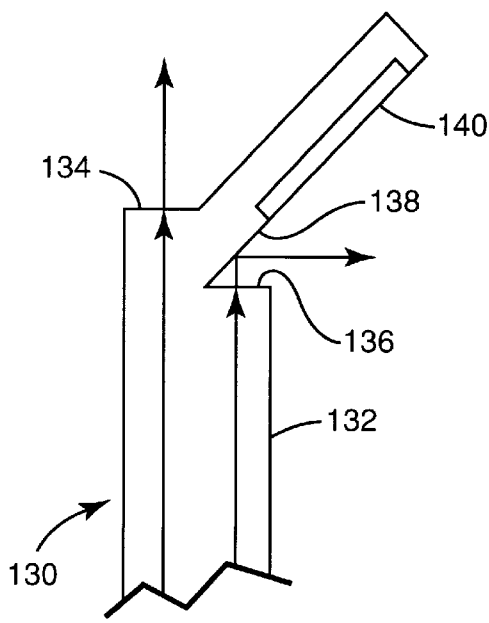
FIG. 18 is a side view of an alternate dental mirror.
Figure 19:
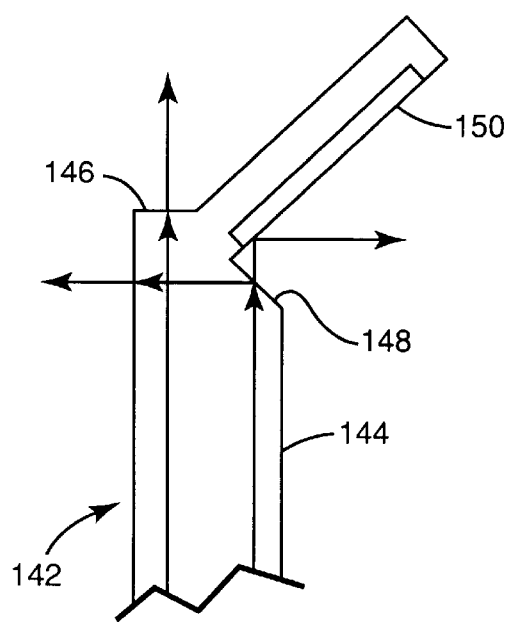
FIG. 19 is a side view of a second alternate dental mirror.

Fourth, it is understood that a variety of dental mirrors other than those illustrated by U.S. Pat. No. 5,139,421 to Verderber may be used with the connector 22. As one example, the dental mirrors shown by U.S. Pat. No. 3,638,013 to Keller may also be used. As another example, dental mirrors can be devised which have a hollow shank to carry light, and light can be transmitted from an aperture at the shank heel. These dental mirrors may also include an aperture at the shank face so that reflected light from inside the hollow shank is emitted from the shank face. As a further example, FIGS. 18 and 19 illustrate dental mirrors with shanks made of translucent material, similar to those of Keller and Verderber, but which do not utilize Verderber's internal reflection strategy to emit light from the shank face. In the dental mirror 130 of FIG. 18, light is transmitted through a translucent shank 132. The light is then emitted through shank heel 134 and shank face 136. After emission from the shank face 136, the light is reflected from the mirror frame 138 below the mirror 140. In the dental mirror 142 of FIG. 19, light is transmitted through transparent shank 144 and emitted through shank heel 146 and shank face 148. The light emitted from shank face 148 is then reflected from the mirror 150.

Fifth, it is understood that the connector 22 may be used with apparata other than mirrors and dental mirrors. As one example, a variety of translucent light-emitting probes are known to the art, and these may be used with the connector 22. As an example, a barrel or loupe including a condensing lens or other type of lens could be inserted at the collet sleeve 38 of the connector 22. When light is piped through the fiberoptic cable 23, the loupe can provide desired focusing or dispersion of the light so that the connector 22 acts as an illuminating wand. Further, the connector 22 may be provided without the handle 68 and used on apparata such as head or body mounted illumination implements to form a quick-release attachment for different mirrors, lenses, and fiberoptic cables. An exemplary apparatus on which the connector 22 is expected to find use is the ZEON illuminator (Orascoptic Research, Madison, WI) described in U.S. patent application Ser. No. 08/447,357, incorporated by reference herein.

It is understood that preferred embodiments of the invention have been described above in order to illustrate how to make and use the invention. The invention is not intended to be limited to these embodiments, but rather is intended to be limited only by the claims set out below. Thus, the invention encompasses all alternate embodiments that fall literally or equivalently within the scope of these claims. It is understood that in the claims, means plus function clauses are intended to encompass the structures described above as performing their recited function, and also both structural equivalents and equivalent structures. As an example, though a nail and a screw may not be structural equivalents insofar as a nail employs a cylindrical surface to secure parts together whereas a screw employs a helical surface, in the context of fastening parts, a nail and a screw are equivalent structures.

What is claimed is:

1. A cable connector comprising:
   a. a sleeve having a tip, a tail, and an internal sleeve surface defining a tube insertion passage therein,
   b. a tube including an implement engagement portion, a cable engagement portion, and an internal tube surface defining a cable passage extending through the implement engagement portion and cable engagement portion, the implement engagement portion including at least two resiliently flexible tongues extending therefrom, the cable engagement portion including a resiliently flexible finger extending therefrom and terminating in a floating finger end, wherein the insertion of the tube into the tube insertion passage of the sleeve abuts the internal sleeve surface against both the tongues and the floating finger end, thereby biasing the tongues and floating finger end inwardly toward the axis of the tube.

2. The cable connector of claim 1 wherein the floating finger end rests within the cable passage when the finger is unbiased.

3. The cable connector of claim 1 wherein the floating finger end rests outside the cable passage when the finger is unbiased.

4. The cable connector of claim 1 wherein the internal tube surface includes a narrowed throat spaced from the floating finger end.

5. The cable connector of claim 4 wherein the floating finger end includes a raised finger projection directed toward the axis of the tube.

6. The cable connector of claim 5 in combination with a fiberoptic cable having an end mounted within a terminal connector, the terminal connector being adapted to snugly fit within the cable passage between the narrowed throat and the raised finger projection.

7. The cable connector of claim 6 in combination with an implement including a light-transmitting shank, the shank resting within the cable passage and between the tongues.

8. The cable connector of claim 1 further comprising attachment means for fixing the sleeve about the implement engagement portion and cable engagement portion of the tube.

9. The cable connector of claim 8 wherein the attachment means include complementary threading on the tube and sleeve.

10. The cable connector of claim 1 further comprising a handle extending from the cable engagement portion of the tube.

11. The cable connector of claim 10 wherein the handle includes an aperture situated along the axis of the cable passage of the tube.

12. The cable connector of claim 1 wherein the implement engagement portion is spaced from the cable engagement portion along the length of the tube.

13. A cable connector comprising:
a. a tube including a resiliently flexible finger and at least two resiliently flexible tongues spaced from the finger along the length of the tube, the finger and tongues being bendable in a radial direction with respect to the tube,
b. a sleeve including an internal sleeve surface defining a tube insertion passage therein,
c. a fiberoptic cable within the tube,
d. an implement including a light-transmitting shank, the shank resting within the tube and between the tongues,
wherein the insertion of the tube into the tube insertion passage of the sleeve moves the both the tongues and the floating finger end into abutment with the internal sleeve surface, thereby biasing the tongues inwardly against the shank and also biasing the finger against the fiberoptic cable.

14. The cable connector of claim 13 wherein the finger includes a terminal finger end unconnected to the tube, the finger end including a raised finger projection directed radially inward toward the axis of the tube,
and further wherein the fiberoptic cable includes a discontinuity engageable by the finger projection.

15. The cable connector of claim 14 wherein the discontinuity is a barrel, and wherein the interior of the tube includes a narrowed throat spaced from the raised finger projection, and further wherein the discontinuity is a barrel sized to fit between the raised finger projection and the narrowed throat.

16. The cable connector of claim 13 further comprising a handle connected to the tube.

17. The cable connector of claim 13 wherein the fiberoptic cable extends through at least a portion of the handle.

18. A cable connector comprising:
a. a sleeve having an internal sleeve surface defining a tube insertion passage therein,
b. a tube including:
(1) at least two resiliently flexible tongues,
(2) at least one resiliently flexible ringer,
(3) an internal tube surface defining a cable passage, and
(4) a handle generally coaxial with the cable passage;
wherein the insertion of the tube into the tube insertion passage of the sleeve abuts the internal sleeve surface against both the tongues and each finger, thereby biasing the tongues and each finger inwardly toward the axis of the tube;
c. a fiberoptic cable within the cable passage adjacent each finger, and
d. an implement including a light-transmitting shank resting within the cable passage and between the tongues.

19. A cable connector comprising:
a. a sleeve having an internal sleeve surface defining a tube insertion passage therein,
b. a tube including:
(1) at least two resiliently flexible tongues,
(2) at least one resiliently flexible finger,
(3) an internal tube surface defining a cable passage, wherein the internal tube surface includes a narrowed throat between the tongues and each finger, and
(4) a handle generally coaxial with the cable passage;
wherein the insertion of the tube into the tube insertion passage of the sleeve abuts the internal sleeve surface against both the tongues and each finger, thereby biasing the tongues and each finger inwardly toward the axis of the tube.

20. The cable connector of claim 19 wherein the finger includes a raised finger projection directed toward the axis of the tube, the raised finger projection being spaced from the narrowed throat.

21. A cable connector comprising:
a. a sleeve having an internal sleeve surface defining a tube insertion passage therein,
b. a tube including:
(1) at least two resiliently flexible tongues,
(2) at least one resiliently flexible finger, wherein the finger is spaced from the tongues along the length of the tube,
(3) an internal tube surface defining a cable passage, and
(4) a handle generally coaxial with the cable passage;
wherein the insertion of the tube into the tube insertion passage of the sleeve abuts the internal sleeve surface against both the tongues and each finger, thereby biasing the tongues and each finger inwardly toward the axis of the tube.

* * * * *